(12) United States Patent
Trousset et al.

(10) Patent No.: US 10,524,865 B2
(45) Date of Patent: Jan. 7, 2020

(54) COMBINATION OF 3D ULTRASOUND AND COMPUTED TOMOGRAPHY FOR GUIDANCE IN INTERVENTIONAL MEDICAL PROCEDURES

(71) Applicant: General Electric Company, Schenectady, NY (US)

(72) Inventors: Yves L. Trousset, Palaiseau (FR); Maxime Taron, Buc (FR); Stephan Haulon, Lille (FR)

(73) Assignee: General Electric Company, Schenectady, NY (US)

( * ) Notice: Subject to any disclaimer, the term of this patent is extended or adjusted under 35 U.S.C. 154(b) by 333 days.

(21) Appl. No.: 15/381,629

(22) Filed: Dec. 16, 2016

(65) Prior Publication Data

US 2018/0168732 A1    Jun. 21, 2018

(51) Int. Cl.
*A61B 6/03*     (2006.01)
*A61B 34/20*    (2016.01)
(Continued)

(52) U.S. Cl.
CPC .............. *A61B 34/20* (2016.02); *A61B 6/032* (2013.01); *A61B 6/504* (2013.01); *A61B 6/5211* (2013.01);
(Continued)

(58) Field of Classification Search
CPC ....... A61B 34/20; A61B 6/032; A61B 6/5235; A61B 6/5247; A61B 8/483; A61B 8/5261; A61B 2090/3762; A61B 2090/378
See application file for complete search history.

(56) References Cited

U.S. PATENT DOCUMENTS 9,155,470 B2    10/2015  Grbic et al.
2008/0085042 A1*  4/2008  Trofimov ............... A61B 5/042
                                                    382/128
(Continued)

OTHER PUBLICATIONS

Brekken et al., "Ultrasound in Abdominal Aortic Aneurysm", Diagnosis, Screening and Treatment of Abdominal, Thoracoabdominal and Thoracic Aortic Aneurysms, R.T. Grundmann ed, 2011, 23 pages.

(Continued)

Primary Examiner — Eric D. Bertram
(74) Attorney, Agent, or Firm — Boyle Fredrickson, S.C.

(57) ABSTRACT

In the present invention, an imaging system and method is provided to obtain a fusion image of a patient anatomy used as a navigational 3D roadmap to guide an interventional device into the anatomy. The fusion image fuses in real-time, fluoroscopy images taken during the interventional procedure with pre-operative CTA images, so that the operator can see the anatomy in the fluoroscopy image without having to inject contrast agent. To correct for the deformation in the anatomy from the pre-op CTA images form the insertion of interventional devices during the procedure, a 3D ultrasound image is obtained after the insertion of the devices. The 3D ultrasound images are then utilized to correct the pre-op CTA images and provide the current vascular anatomy of the patient. This updated CTA image is fused with the intra-op fluoro images to provide an accurate 3D roadmap image that matches the deformed anatomy.

14 Claims, 3 Drawing Sheets

(51) Int. Cl.
*A61B 90/00* (2016.01)
*A61B 6/00* (2006.01)
*A61B 8/08* (2006.01)

(52) U.S. Cl.
CPC ............ *A61B 8/0841* (2013.01); *A61B 8/483* (2013.01); *A61B 90/37* (2016.02); *A61B 2034/2065* (2016.02); *A61B 2090/378* (2016.02); *A61B 2090/3762* (2016.02)

(56) References Cited

U.S. PATENT DOCUMENTS

| | | | |
|---|---|---|---|
| 2008/0095421 A1* | 4/2008 | Sun | A61B 6/12 382/131 |
| 2008/0283771 A1* | 11/2008 | Li | A61B 6/463 250/459.1 |
| 2013/0279780 A1* | 10/2013 | Grbic | A61B 5/0033 382/131 |

OTHER PUBLICATIONS

Kaspersen et al., "Three-Dimensional Ultrasound-Based Navigation Combined with Preoperative CT During Abdominal Interventions: A Feasibility Study", Cardiovasc Intervent Radiol (2003) 26:347-356.

* cited by examiner

COMBINATION OF 3D ULTRASOUND AND COMPUTED TOMOGRAPHY FOR GUIDANCE IN INTERVENTIONAL MEDICAL PROCEDURES

FIELD OF THE INVENTION

The invention relates generally to tracking or delivery of medical instruments in a medical procedure, and in particular, systems and methods to track and deliver medical instruments to accommodate for deformations in patient anatomy caused during the medical procedure.

BACKGROUND OF INVENTION

Image-guided surgery is a developing technology that allows surgeons to perform an intervention or a surgery in a minimally invasive way while being guided by images, which may be "real" images or virtual images. For instance, in laparoscopic surgery, a small video camera is inserted through a small incision made in the patient skin. This video camera provides the operator with a "real" image of the anatomy. In other types of image-guided surgery, such as endo-vascular surgery where a lesion is treated with devices inserted through a catheter navigated into the arteries of the patient, are "image-guided" because low dose x-ray images (also called fluoroscopy images) are used to guide the catheters and the devices through the patient anatomy. The fluoroscopy image is a "real" image, not a virtual image, as it is obtained using real X-rays and shows the real anatomy of the patient. Then there are also cases where a "virtual" image" is used, which is a combination of real images utilized to form the virtual image of the anatomy in a known manner. An example of image-guided surgery using both "real" and "virtual" images is the minimally invasive surgery of spine, where "real" fluoroscopy images acquired during the surgery are used to guide the insertion of devices in the vertebras, while pre-operative CT or Cone-beam CT (CBCT) images are also used, in conjunction with surgical navigation systems, to visualize the location of the devices in the 3D anatomy of the patient. Because the display of the location of the devices in the CT or CBCT images does not result of a direct image acquisition performed during the surgery, as there is not a CT in the operating room, but from a combination of pre-existing real images and information provided by the surgical navigation system, the display of the device location in the CT or CBCT images is described as a "virtual" image.

Regardless of particular images utilized in its formation, image-guided surgery allows the surgeon to reduce the size of entry or incision into the patient, which can minimize pain and trauma to the patient and result in shorter hospital stays. Examples of image-guided procedures include laparoscopic surgery, thoracoscopic surgery, endoscopic surgery, etc. Types of medical imaging systems, for example, radiologic imaging systems, computerized tomography (CT), magnetic resonance imaging (MRI), positron emission tomography (PET), ultrasound (US), X-ray angiography machines, etc., can be useful in providing static image guiding assistance to medical procedures. The above-described imaging systems can provide two-dimensional or three-dimensional images that can be displayed to provide a surgeon or clinician with an illustrative map to guide a tool (e.g., a catheter) through an area of interest of a patient's body.

In clinical practice, minimally invasive percutaneous cardiac and vascular interventions are becoming more prevalent as compared with traditional open surgical procedures. Such minimally invasive percutaneous cardiac and vascular interventions have advantages of shorter patient recovery times, as well as faster and less risky procedures. In such minimally invasive cardiac and vascular interventions, devices such as stents or stent grafts are delivered into the patient through vessels via a catheter. Navigating the catheter inside the vessels of a patient is challenging. To assist in the navigation, X-ray fluoroscopy is typically used to visualize the catheter during the procedure. However, this imaging modality does not capture soft tissue structure of the patient well.

In particular, during one exemplary type of cardiac and vascular interventional procedure, i.e., an endo-vascular aneurysm repair (EVAR) procedure, the operator inserts and deploys an endograft in the aorta under fluoroscopy guidance. To achieve this task, the operator needs obviously to see the devices, which is easily achieved using fluoroscopy, but he/she also needs to understand the location of the devices versus the vascular anatomy, which is more challenging.

Since the arteries are not spontaneously visible under fluoroscopy, X-ray sequences taken after injection of a contrast agent have to be acquired to visualize the arteries. However the use of the contrast agent has a number of significant drawbacks. First, the contrast agent requires a significant time to become effective and has a limited time for effectiveness within the patient before additional contrast medium is require. Second, the contrast agent can have certain adverse effects on the patient in larger amounts, such as required for multiple X-ray sequences, including the contribution to the potential development of patient nephropathy as a result of the amount of contrast agent being injected. Third, the increased number of X-ray sequences necessarily increases the total X-ray exposure to both patient and staff as a result of the multiple X-ray sequences being taken.

More recently, solutions based on the fusion of a pre-operative 3D computed tomography angiography (CTA) image that shows the anatomy of the patient through which the interventional tool is to be navigated with the fluoroscopy images have been recently proposed to improve the EVAR guidance. In this process, as shown in FIG. 1, a pre-op CTA image 1000 is obtained and subsequently registered or fused with an intra-operative fluoro or X-ray image 1002, such as by overlaying the fluoro image onto the CTA image or vice versa, to illustrate a fusion image 1004 illustrating both the structure of the anatomy of the patient and the current location of the interventional tool, e.g., a guide wire or catheter, within the anatomy. These fusion image solutions can more clearly illustrate the interventional tool location within the patient anatomy, and have been shown to contribute to the reduction of both the volume of injected contrast agent and the X-ray exposure to the patient.

However, one significant drawback of the fusion image solution for interventional procedures, such as an EVAR procedure, is that the insertion of the interventional devices themselves during the interventional procedure deforms the anatomy of the aorta, and in particular straightens the aorta thereby moving the location of the ostia of visceral arteries from the anatomy illustrated in the pre-op CTA images. As a consequence, after insertion of the interventional device, the anatomy depicted by the pre-op CTA image no longer matches the current patient anatomy and cannot provide an accurate roadmap for the navigation of the device through the anatomy.

To solve this anatomy deformation issue, the operator has to acquire an x-ray based 2D digital subtraction angiography (DSA) series after insertion of the device(s) and use this DSA series to manually correct for the deformation of the aorta. This solution for deformation correction is sub-optimal for two reasons. First, it utilizes an injection of contrast agent to the patient, which is directly contradictory to one of the objectives of 3D roadmap/fusion image, which is to reduce the amount of contrast agent required to be injected into the patient. Second, the final registration accuracy provided by the DSA correction may still be limited. Since the deformation of the anatomy takes place in 3D, it is not possible, from just one 2D DSA acquired in one angulation, to find a correction that would adequately reflect deformations for the ostia of all visceral arteries.

One additional solution has been the combination of CT images with ultrasound images to identify changes in the positioning of fiducial and anatomical landmarks in the images of the patient anatomy. For example, in prior art combined CT/ultrasound imaging methods, such as that disclosed in Kaspersen et. al., *Three-Dimensional Ultrasound-Based Navigation Combined with Preoperative CT During Abdominal Interventions: A Feasibility Study*, Cardiovasc Intervent Radiol (2003) 26:347-356, separate pre-op CT images are compared with intra-op ultrasound images to compare the position of fiducial and/or anatomical landmarks in order to determine the differences between the anatomy illustrated in the CT image and in the ultrasound image by illustrating the images side-by-side or by overlaying the images with one another. These differences are then utilized by the physician to interpret the current configuration for the patient anatomy in order to perform the interventional procedure.

However, while this image combination provides the physician with the ability to interpret the differences in the displayed anatomies, it is completely left to the experience and discretion of the physician to utilize the displayed information to identify the location and extent of any deformations in the displayed patient anatomy in each if the respective CT and ultrasound images. When this is done during an interventional procedure by directly comparing the CT and ultrasound images, this requires the physician to make decision on potentially incomplete information and to do so by taking focus off of the procedure being performed, both of which are undesirable.

As a result, it is desirable to develop an imaging system and method that can improve upon existing systems and methods for the correction of anatomy deformation in interventional procedures, such as EVAR procedures.

BRIEF DESCRIPTION OF THE INVENTION

The above-mentioned drawbacks and needs are addressed by the embodiments described herein in the following description.

According to one aspect of an exemplary embodiment of the invention, an imaging system is utilized to obtain a fusion image of the anatomy, e.g., the aorta in an EVAR procedure, of a patient in order to provide a navigational roadmap of for the insertion of an interventional tool, e.g., a guide wire or catheter, into the anatomy. The technology for creation of the fusion image fuses in a known manner and in real-time, radiologic images, such as fluoroscopy images taken during the interventional procedure with pre-operative CTA images, so that the operator can see the aorta and the visceral vessels in the fluoroscopy image without having to inject contrast agent. To correct for the deformation in the vascular anatomy from the pre-op CTA images created by the endovascular devices that are used during an EVAR procedures, a 3D ultrasound image of the aorta is additionally acquired during the EVAR procedure after the insertion of the devices. The 3D ultrasound image can be acquired with a standard ultrasound sensor located outside of the patient, or with an ultrasound sensor inserted directly inside the aorta and called "intra-vascular ultrasound" (IVUS). The 3D ultrasound images are then utilized to correct the pre-op CTA images and provide the current vascular anatomy of the patient. This corrected CTA image is then combined or fused with the intra-op fluoro images taken during the procedure to provide an accurate 3D roadmap image that better matches the deformed anatomy of the aorta for proper performance of the procedure.

According to still a further aspect of one exemplary embodiment of the invention, a method for updating a pre-operative image of a patient anatomy with an intra-operative image of the patient anatomy obtained during an interventional medical procedure includes the steps of obtaining a pre-operative first image volume of the patient anatomy utilizing a first imaging system modality, obtaining an intra-operative second image volume of the patient anatomy utilizing a second imaging system modality, identifying a number of landmarks in each of the first image volume and the second image volume and modifying the first image volume according to differences in the position of the number of landmarks between the first image volume and the second image volume to form an updated image volume.

According to still a further aspect of one exemplary embodiment of the invention, a method for updating a pre-operative CTA image to accommodate for patient anatomy deformation in an intra-operative procedure to provide an intra-operative 3D roadmap includes the steps of obtaining a pre-operative 3D CTA image volume of the patient anatomy, obtaining an intra-operative 3D ultrasound image volume of the patient anatomy, identifying a number of landmarks in each of the 3D CTA volume and the 3D ultrasound image volume and modifying the 3D CTA volume according to differences in the position of the number of landmarks between the 3D CTA volume and the 3D ultrasound image volume to form an updated 3D CTA image volume.

According to still a further aspect of one exemplary embodiment of the invention, an imaging system for obtaining a pre-operative first image volume in a first imaging modality and an intra-operative second image volume in a second modality for an interventional medical procedure in order to update the first image volume includes a first imaging system for obtaining the pre-operative first image volume, a second imaging system for obtaining the intra-operative second image volume, an image processing module operably connected to the first imaging system and to the second imaging system, the image processing module configured to process image data from the first imaging system and the second imaging system to update the first image volume and form an updated image volume, an operator interface connected to the image processing module and a display operably connected to the image processing module to display at least one of the first image volume, the second image volume and the updated image volume.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The drawings illustrate the best mode presently contemplated of carrying out the disclosure. In the drawings.

DETAILED DESCRIPTION

Figure 1:
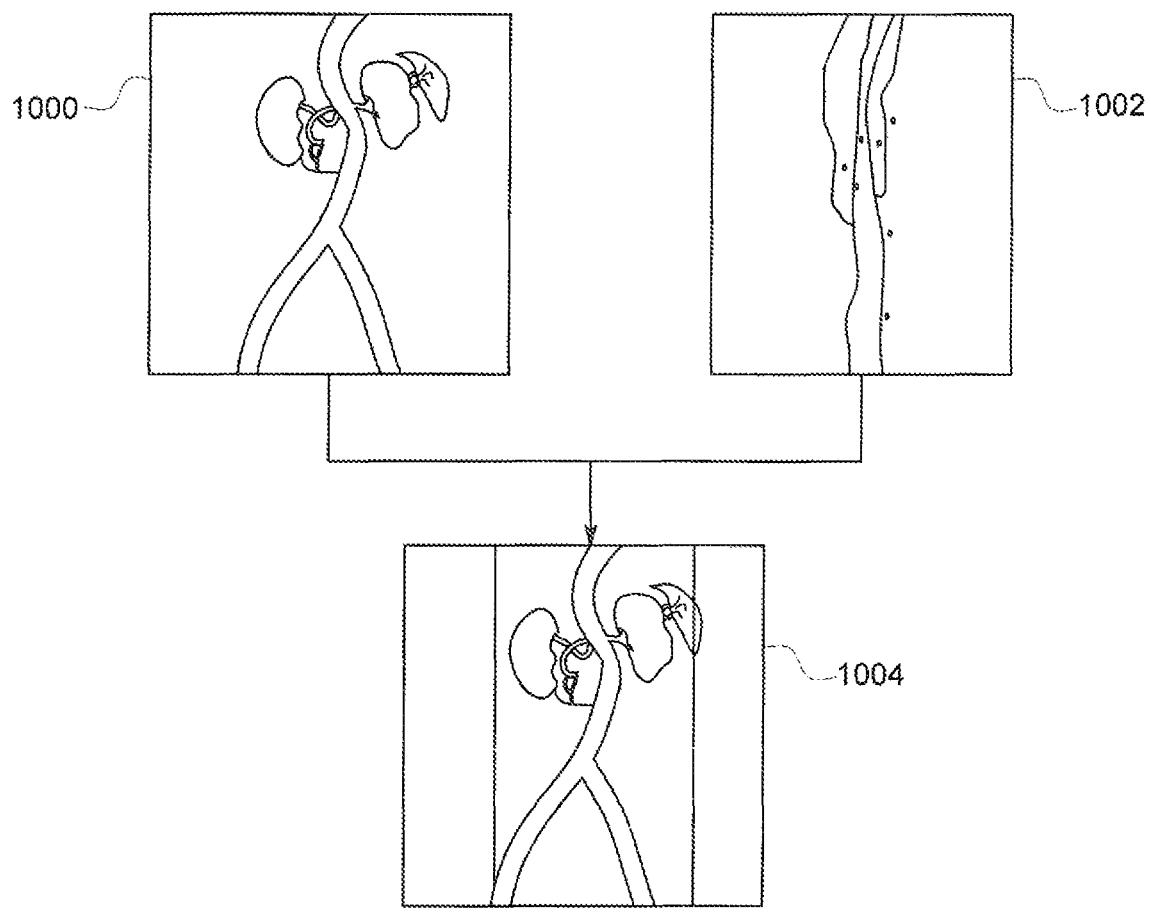
FIG. 1 is a diagrammatic representation of a prior art fusion imaging process.
Figure 2:
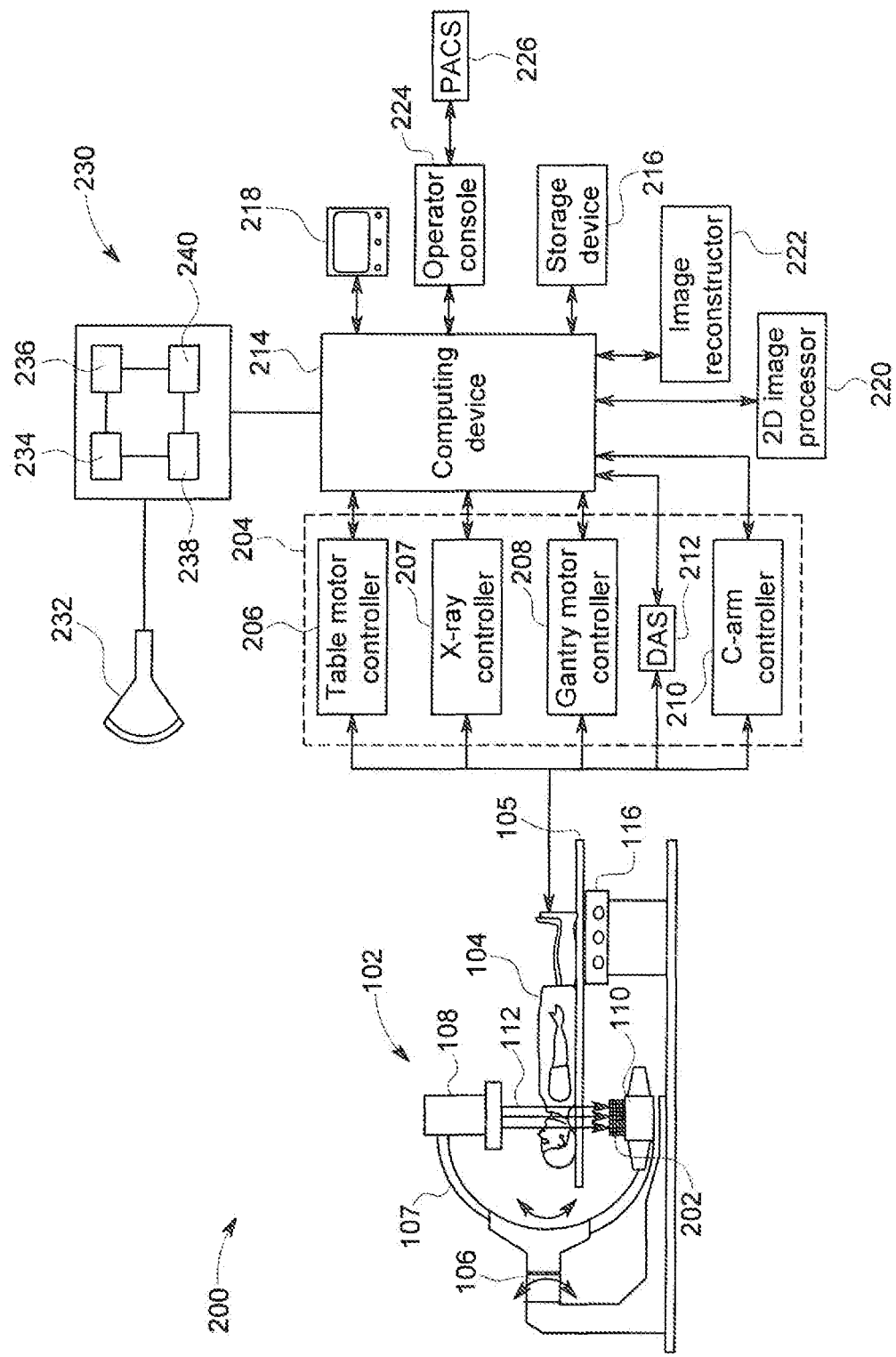
FIG. 2 is a schematic drawing of a combined imaging system according to one exemplary embodiment of the invention.

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

The following description presents embodiments of systems and methods for imaging patient anatomy in real-time during interventional and/or surgical procedures. Particularly, certain embodiments describe systems and methods for imaging processes for updating images illustrating the patient anatomy during minimally-invasive interventional procedures. The interventional procedures, for example, may include angioplasty, stent placement, removal of blood clots, localized thrombolytic drug administration, perfusion studies, balloon septostomy, Transcatheter Aortic-Valve Implantation (TAVI), EVAR, tumor embolization and/or an electrophysiology study.

It may be noted that in the present description, the terms "dynamic process(s)" and "transient phenomena" have been used interchangeably to refer to processes and events where at least a portion of the subject to be imaged exhibits motion or other dynamic processes over time, such as, movement of an interventional device through a vascular structure. By way of example, the dynamic processes may include fluid flow through a passage, device vibrations, take-up and wash-out of a contrast medium, cardiac motion, respiratory motion, peristalsis, and/or change in tissue perfusion parameters including regional blood volume, regional mean transit time and/or regional blood flow.

Additionally, the following description presents embodiments of imaging systems, such as radiologic imaging systems, and methods that minimize contrast agent dosage, x-ray radiation exposure and scan durations. Certain embodiments of the present systems and methods may also be used for reconstructing high-quality 3D cross-sectional images in addition to the 2D projection images for allowing diagnosis, therapy delivery, and/or efficacy assessment.

For discussion purposes, embodiments of the present systems are described with reference to use of a C-arm system employing conventional and unconventional acquisition trajectories for imaging a target region of the subject. In certain embodiments, the present systems and methods may be used during interventional or surgical procedures. Additionally, embodiments of the present systems and methods may also be implemented for imaging various transient phenomena in non-medical imaging contexts, such as security screening and/or industrial nondestructive evaluation of manufactured parts. An exemplary system that is suitable for practicing various implementations of the present technique is described in the following section with reference to FIG. 1.

FIG. 1 illustrates an exemplary radiologic imaging system 200, for example, for use in interventional medical procedures. In one embodiment, the system 200 may include a C-arm radiography system 102 configured to acquire projection data from one or more view angles around a subject, such as a patient 104 positioned on an examination table 105 for further analysis and/or display. To that end, the C-arm radiography system 102 may include a gantry 106 having a mobile support such as a movable C-arm 107 including at least one radiation source 108 such as an x-ray tube and a detector 110 positioned at opposite ends of the C-arm 107. In exemplary embodiments, the radiography system 102 can be an x-ray system, a positron emission tomography (PET) system, a computerized tomosynthesis (CT) system, an angiographic or fluoroscopic system, and the like or combination thereof, operable to generate static images acquired by static imaging detectors (e.g., CT systems, MRI systems, etc.) prior to a medical procedure, or real-time images acquired with real-time imaging detectors (e.g., angioplastic systems, laparoscopic systems, endoscopic systems, etc.) during the medical procedure, or combinations thereof. Thus, the types of acquired images can be diagnostic or interventional.

In certain embodiments, the radiation source 108 may include multiple emission devices, such as one or more independently addressable solid-state emitters arranged in one or multi-dimensional field emitter arrays, configured to emit the x-ray beams 112 towards the detector 110. Further, the detector 110 may include a plurality of detector elements that may be similar or different in size and/or energy sensitivity for imaging a region of interest (ROI) of the patient 104 at a desired resolution.

In certain embodiments, the C-arm 107 may be configured to move along a desired scanning path for orienting the x-ray source 108 and the detector 110 at different positions and angles around the patient 104 for acquiring information for 3D imaging of dynamic processes. Accordingly, in one embodiment, the C-arm 107 may be configured to rotate about a first axis of rotation. Additionally, the C-arm 107 may also be configured to rotate about a second axis in an angular movement with a range of about plus or minus 60 degrees relative to the reference position. In certain embodiments, the C-arm 107 may also be configured to move forwards and/or backwards along the first axis and/or the second axis.

Accordingly, in one embodiment, the C-arm system 102 may include control circuitry 114 configured to control the movement of the C-arm 107 along the different axes based on user inputs and/or protocol-based instructions. To that end, in certain embodiments, the C-arm system 102 may include circuitry such as tableside controls 116 that may be configured to provide signals to the control circuitry 114 for adaptive and/or interactive control of imaging and/or processing parameters using various input mechanisms. The imaging and/or processing parameters, for example, may include display characteristics, x-ray technique and frame rate, scanning trajectory, table motion and/or position, and gantry motion and/or position.

In certain embodiments, the detector 110 may include a plurality of detector elements 202, for example, arranged as a 2D detector array for sensing the projected x-ray beams 112 that pass through the patient 104. In one embodiment, the detector elements 206 produce an electrical signal representative of the intensity of the impinging x-ray beams 112, which in turn, can be used to estimate the attenuation of the x-ray beams 112 as they pass through the patient 104. In another embodiment, the detector elements 202 determine a count of incident photons in the x-ray beams 112 and/or determine corresponding energy.

Particularly, in one embodiment, the detector elements 202 may acquire electrical signals corresponding to the generated x-ray beams 112 at a variety of angular positions around the patient 104 for collecting a plurality of radiographic projection views for construction of X-ray images, such as to form fluoro image(s). To that end, control circuitry 114 for the system 200 may include a control mechanism 204 configured to control position, orientation and/or rotation of the table 105, the gantry 106, the C-arm 107 and/or the components mounted thereon in certain specific acquisition trajectories.

The control mechanism 204, for example, may include a table motor controller 206, which allows control of the position and/or orientation of the table 105 based on a protocol-based instruction and/or an input received from the physician, for example, via tableside controls, such as a joystick. During an intervention, for example, the physician may grossly position an interventional device in the patient 104 in the field of view of the system 102 by moving the table 105 using the table motor controller 206. Once the interventional device can be visualized, the physician may advance position of the interventional device within the vasculature and performs a diagnostic procedure or a therapeutic procedure.

In certain embodiments, the x-ray source 108 and the detector 110 for interventional imaging may be controlled using an x-ray controller 207 in the control mechanism 204, where the x-ray controller 207 is configured to provide power and timing signals to the radiation source 108 for controlling x-ray exposure during imaging. Further, the control mechanism 204 may also include a gantry motor controller 208 that may be configured to control the rotational speed, tilt, view angle, and/or position of the gantry 106. In certain embodiments, the control mechanism 204 also includes a C-arm controller 210, which in concert with the gantry motor controller 208, may be configured to move the C-arm 107 for real-time imaging of dynamic processes.

In one embodiment, the control mechanism 204 may include a data acquisition system (DAS) 212 for sampling the projection data from the detector elements 206 and converting the analog data to digital signals for image reconstruction by 2D image processor 220, for reconstructing high-fidelity 2D images in real-time for use during the interventional procedure, and/or 3D image processor/reconstructor 222, for generating 3D cross-sectional images (or 3D volumes), and subsequent illustration of the images on display 218. Moreover, in certain embodiments, the data sampled and digitized by the DAS 212 may be input to a computing device 214. Alternatively, in certain embodiments, the computing device 214 may store the projection data in a storage device 216, such as a hard disk drive, a floppy disk drive, a compact disk-read/write (CD-R/W) drive, a Digital Versatile Disc (DVD) drive, a flash drive, or a solid-state storage device for further evaluation.

In one embodiment, the system 200 may include an operator console 224 that may be configured to allow selection and display of scanning modes, FOV, prior exam data, and/or intervention path. The operator console 224 may also allow on-the-fly access to 2D and 3D scan parameters and selection of an ROI for subsequent imaging, for example, based on operator and/or system commands.

Further, in certain embodiments, the system 200 may be coupled to multiple displays, printers, workstations, a picture archiving and communications system (PACS) 226 and/or similar devices located either locally or remotely, for example, within an institution or hospital, or in an entirely different location via communication links in one or more configurable wired and/or wireless networks such as a hospital network and virtual private networks.

In addition to the C-arm system 102, the imaging system 200 additionally includes an ultrasound imaging system 230 operably connected to the computing device 214. The ultrasound imaging system 230 includes an ultrasound probe 232 connected to the system 230 and capable of obtaining images utilized to acquire a 3D ultrasound image of the patient anatomy. In particular exemplary embodiments, the ultrasound system 230 can produce a 3D ultrasound image utilizing a 3D ultrasound probe, which can be an external or internal (intra-vascular) ultrasound probe, or with a regular 2D ultrasound probe which is navigated, i.e. equipped with navigation sensors providing, in real-time, the location and orientation of the probe 232 in order to enable the 2D images to be processed into a 3D ultrasound image volume of the patient anatomy.

The ultrasound system 230 also includes a system controller 234 that includes a plurality of modules. The system controller 234 is configured to control operation of the ultrasound system 230. For example, the system controller 234 may include an image-processing module 236 that receives the ultrasound signals (e.g., RF signal data or IQ data pairs) and processes the ultrasound signals to generate frames of ultrasound information (e.g., ultrasound images) for displaying to the operator. The image-processing module 236 may be configured to perform one or more processing operations according to a plurality of selectable ultrasound modalities on the acquired ultrasound information. By way of example only, the ultrasound modalities may include color-flow, acoustic radiation force imaging (ARFI), B-mode, A-mode, M-mode, spectral Doppler, acoustic streaming, tissue Doppler module, C-scan, and elastography. The generated ultrasound images may be two-dimensional (2D), three-dimensional (3D) or four-dimensional (4D).

Acquired ultrasound information may be processed in real-time during an imaging session (or scanning session) as the echo signals are received. Additionally or alternatively, the ultrasound information may be stored temporarily in the memory 238 during an imaging session and processed in less than real-time in a live or off-line operation. An image memory 240 is included for storing processed frames of acquired ultrasound information that are not scheduled to be displayed immediately. The image memory 240 may comprise any known data storage medium, for example, a permanent storage medium, removable storage medium, and the like.

In operation, the ultrasound system 230 acquires data, for example, volumetric data sets by various techniques (e.g., 3D scanning, real-time 3D imaging, volume scanning, 2D scanning with transducers having positioning sensors, freehand scanning using a voxel correlation technique, scanning using 2D or matrix array transducers, and the like). Ultrasound images are displayed to the operator or user of the ultrasound system 230 on the display device 218.

Figure 3:
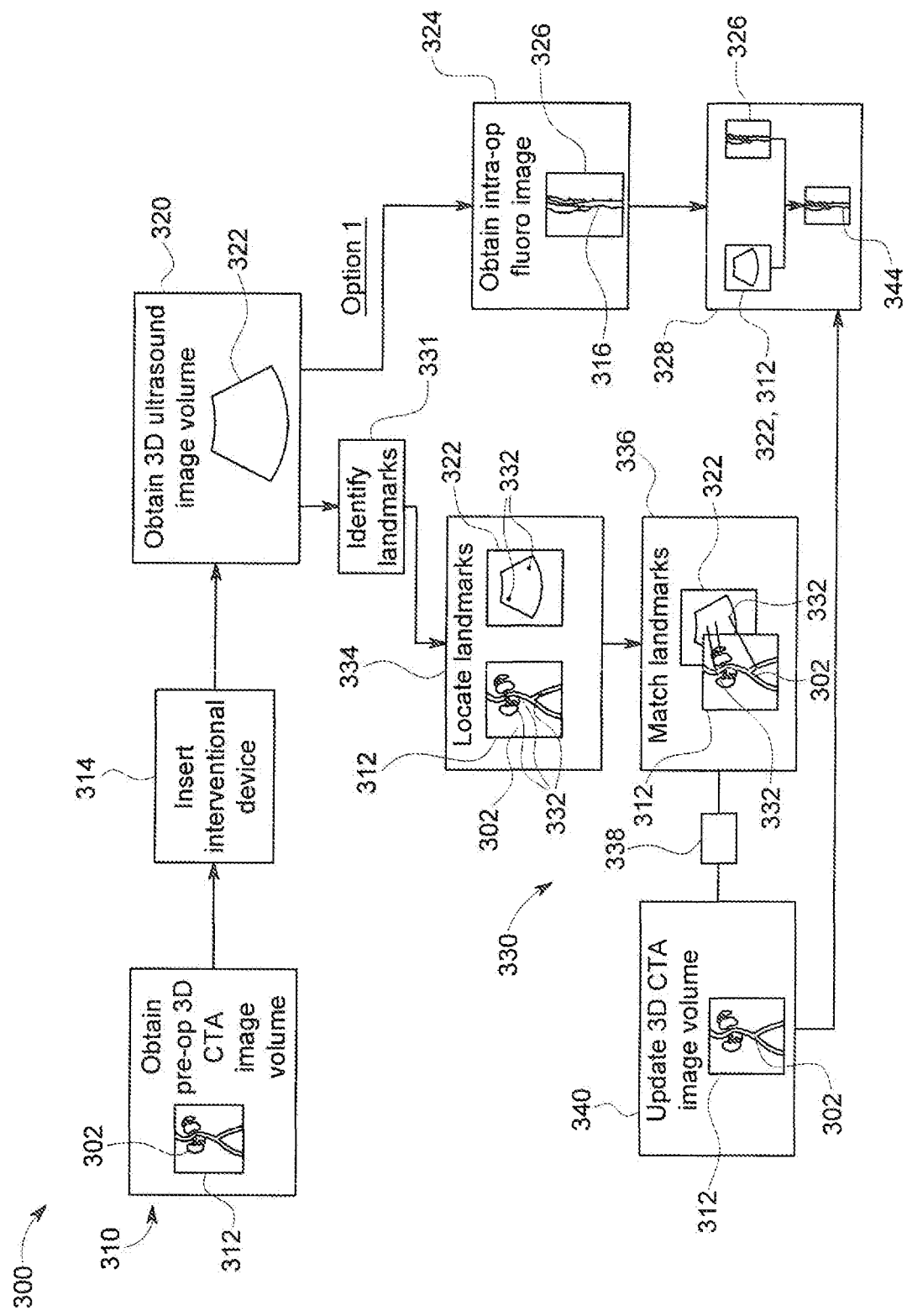
FIG. 3 is a diagrammatic representation of fusion imaging method according to an exemplary embodiment of the invention.

Having provided a description of the general construction of the system 200, the following is a description of a method 300 (see FIG. 3) of operation of the system 200 in relation to the imaged patient anatomy 302. Although an exemplary embodiment of the method 300 is discussed below, it should be understood that one or more acts or steps comprising the method 300 could be omitted or added. It should also be understood that one or more of the acts can be performed simultaneously or at least substantially simultaneously, and the sequence of the acts can vary. Furthermore, it is embodied that at least several of the following steps or acts can be represented as a series of computer-readable program instructions to be stored in the memory 216,238 for execution by the control circuitry/computing device 114,214 for one or more of the radiography imaging system 102 and/or the ultrasound imaging system 230.

In the method 300, in step 310, initially a pre-op image/volume 312, such as pre-op CTA image/volume, is obtained of the patient anatomy 302. The CTA image/volume 312 is obtained in any suitable imaging manner using the system 102. In step 314, the interventional instrument 316, e.g., the guide wire, is inserted into the patient anatomy 302 during the interventional procedure. Once the interventional device 316 is positioned within the anatomy 302, in step 320 a 3D ultrasound image volume 322 of the anatomy 302, e.g., the aorta during an EVAR procedure, is obtained utilizing the ultrasound system 230.

Once obtained, in an exemplary embodiment of the invention, two options are available for the utilization of the 3D ultrasound image volume 322 of the patient anatomy 302 depending upon the quality of the image 322. First, if the 3D image is of high quality, and clearly shows the various structures of the patient anatomy 302, e.g., the aorta and surrounding tissues and blood vessels, relevant to the procedure, including the deformation of the patient anatomy 302 caused by the insertion of the interventional device 316, the 3D image 322 can be utilized in place of the pre-op CTA image 312 to provide an updated 3D image volume 312' for image fusion. In an initial step 324 of the image fusion, using the C-arm system 102 an intraoperative X-ray image, e.g., fluoro image 326 is obtained of the patient anatomy 302 with the interventional device 316 positioned herein in order to obtain a clear image of the location of the interventional device 316 within the anatomy 302. The fluoro image 326 is then overlaid or fused with the 3D ultrasound image 322 in step 328 to provide a 3D roadmap image of the interventional device 316 within the patient anatomy 302, giving the physician a clear image of both the position of the device 316 and the deformed state of the anatomy 302 resulting from the placement of the interventional device 316 within the anatomy 302. The overlaying or registration of the 3D ultrasound image 322 and the fluoro image 326 can be performed in any suitable and well-known manner.

If the 3D ultrasound image 322 obtained in step 320 is not of high enough quality to be utilized in place of the pre-op CTA image/volume 312, the second option is to fuse the 3D ultrasound image 322 with the pre-op CTA image 312 to measure and/or determine the deformation of the anatomy 302 in the pre-op CTS image 312. This fusion process 330 takes place prior to obtaining the intra-op fluoro image 326 and involves as a first step in block 331 the identifying a number of anatomical landmarks 332 or other identifying portions of the patient anatomy 302 present in both the pre-op CTA image 312 and the 3D ultrasound image 322. These landmarks 332 are specific to the particular patient anatomy 302 being imaged and can be selected automatically or manually. For the exemplary embodiment of providing of guidance and/or a 3D roadmap for an EVAR procedure, the landmarks 332 can be selected to be location(s) of the aortic vascular anatomy, such as for instance the 3D locations of the ostia of the visceral arteries, and in particular the left and right renal arteries, the superior mesenteric artery and the celiac trunk, the aorto-iliac bifurcation, the iliac bifurcations, and the center lines of the aorta and of the other arteries among others. The location of these points and/or landmarks 332 is determined in each of the pre-op CTA image 312 and the 3D ultrasound image 322 in an automated or manual manner in step 334. Once determined in each 3D volume 312, 322 the landmarks 332 are matched in each volume 312,322 in step 336. After matching, in step 338 a suitable process, such as a non-linear transformation of the space between the respective landmarks 332 is performed in order to compute or estimate the deformation of the patient anatomy 302 based on the differences between the landmarks 332 in each volume 312, 322. This deformation is then applied in step 340 to the pre-op CTA image volume 312 in order to provide a clear images 312' of the current, deformed patient anatomy 302 resulting from the placement of the interventional device 316 within the anatomy 302.

After deformation of the pre-op images 312 to obtain the updated image/volume 312', in step 342 the deformed or updated image/volume 312' can be overlaid onto the intra-operative X-ray image, e.g., fluoro image 326 obtained in step 328 to provide the 3D roadmap/fusion image 344 of the current, deformed anatomy 302 and the interventional device 316 to the physician. This process can be performed in any suitable manner, such as by placing the updated image volume 312' in registry with the fluoro image 326 to provide the 3D roadmap. Additionally, the method 300 can be performed as often as necessary during the procedure in order to continually provide an updated image 312' of the anatomy 302 for combination with the fluoro images 326 taken during the length of the procedure In this manner the system 200 automatically provides the physician with an updated patient anatomy 3D roadmap via the image 312' including the deformation of the anatomy 302 as determined by the landmarks 332 in the 3D pre-op CTA image 312 and 3D ultrasound images 322 for fusion with each other to automatically identify and illustrate deformation in the patient anatomy 302 and for combination of updated image '312 with intra-op fluoro images 326.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for updating a pre-operative image of a patient anatomy with an intra-operative image of the patient anatomy obtained during an interventional medical procedure, the method comprising the steps of:
   obtaining a pre-operative first image volume of the patient anatomy utilizing a first imaging system modality;
   obtaining an intra-operative second image volume of the patient anatomy utilizing a second imaging system modality;

identifying a number of landmarks in each of the first image volume and the second image volume;

modifying the first image volume according to differences in the position of the number of landmarks between the first image volume and the second image volume to form an updated image volume, obtaining the intra-operative third image of the patient anatomy after forming the updated image volume; and overlaying the updated image volume on the intra-operative third image, wherein the step of obtaining the intra-operative second image volume comprises obtaining an ultrasound image volume of the patient anatomy.

2. The method of claim 1 wherein the step of obtaining the pre-operative first image volume comprises obtaining a computed tomography angiography (CTA) image volume of the patient anatomy.

3. The method of claim 1 wherein the step of obtaining the intra-operative third image comprises obtaining an intra-operative X-ray image.

4. The method of claim 1 wherein the step of modifying the first image volume comprises the steps of:

matching the locations of the number of landmarks in the first image volume and the second image volume; and performing a non-linear transformation of space between the number of landmarks in the first image volume to obtain the updated image volume.

5. The method of claim 4 wherein the patient anatomy is the aorta and surrounding tissue and blood vessels, and the number of landmarks are selected from the group consisting of ostia of the visceral arteries, the aorto-iliac bifurcation, the iliac bifurcations, the center line of the aorta, the center lines of the other vessels, and combinations thereof.

6. The method of claim 4 wherein the interventional medical procedure is selected from the group consisting of angioplasty, stent placement, removal of blood clots, localized thrombolytic drug administration, perfusion studies, balloon septostomy, transcatheter aortic-valve implantation (TAVI), endo-vascular aneurysm repair (EVAR), tumor embolization and electrophysiology studies.

7. The method of claim 1 wherein the step of modifying the first image volume comprises the step of substituting the second image volume for the first image volume.

8. A method for updating a pre-operative CTA image to accommodate for patient anatomy deformation in an intra-operative procedure to provide an intra-operative 3D roadmap, the method comprising the steps of:

obtaining a pre-operative 3D CTA image volume of the patient anatomy;

obtaining an intra-operative 3D ultrasound image volume of the patient anatomy;

identifying a number of landmarks in each of the 3D CTA volume and the 3D ultrasound image volume;

modifying the 3D CTA volume according to differences in the position of the number of landmarks between the 3D CTA volume and the 3D ultrasound image volume to form an updated 3D CTA image volume; and overlaying the updated 3D CTA image volume onto an intra-operative fluoro image obtained after forming the updated 3D CTA image volume to provide a 3D roadmap.

9. The method of claim 8 wherein the step of modifying the 3D CTA image volume to form the update 3D CTA image volume comprises the steps of:

locating each of the number of landmarks in the 3D CTA image volume and the 3D ultrasound image volume;

matching the locations of the number of landmarks in the 3D CTA image volume and the 3D ultrasound image volume; and computing the deformation of spaces between the number of landmarks in the 3D CTA image volume based on differences in locations of the number of landmarks between the 3D CTA image volume and the 3D ultrasound image volume.

10. An imaging system for obtaining a pre-operative first image volume in a first imaging modality and an intra-operative second image volume in a second modality for an interventional medical procedure in order to update the first image volume, the imaging system comprising:

a first imaging system for obtaining the pre-operative first image volume and an intra-operative third image;

a second imaging system for obtaining the intra-operative second image volume; and an image processing module operably connected to the first imaging system and to the second imaging system, the image processing module configured to process image data from the first imaging system and the second imaging system to update the first image volume and form an updated image volume, wherein the second imaging system is an ultrasound imaging system, wherein the first imaging system is operable to obtain an intra-operative third image after forming the undated image volume, and wherein the image processing module is configured to overlay the updated image volume onto the third image.

11. The imaging system of claim 10 wherein the first imaging system is a radiologic imaging system.

12. The imaging system of claim 10 wherein the image processor is configured to:

identify a number of landmarks in each of the first volume and the second image volume;

locate each of the number of landmarks in the first image volume and the second image volume;

match the locations of the number of landmarks in the first image volume and the second image volume; and computing the deformation of spaces between the number of landmarks in the first image volume based on differences in locations of the number of landmarks between the first image volume and the second image volume.

13. The imaging system of claim 10 further comprising an operator interface connected to the image processing module.

14. The imaging system of claim 13 further comprising a display operably connected to the image processing module to display at least one of the first image volume, the second image volume and the updated image volume.

* * * * *

UNITED STATES PATENT AND TRADEMARK OFFICE
CERTIFICATE OF CORRECTION

PATENT NO. : 10,524,865 B2
APPLICATION NO. : 15/381629
DATED : January 7, 2020
INVENTOR(S) : Yves L. Trousset et al.

Page 1 of 1

It is certified that error appears in the above-identified patent and that said Letters Patent is hereby corrected as shown below:

In the Claims

Claim 10, Column 12, Line 32, delete "undated" and substitute therefor -- updated --.

Signed and Sealed this
Sixteenth Day of June, 2020

Andrei Iancu
*Director of the United States Patent and Trademark Office*